(12) United States Patent
Kussendrager et al.

(10) Patent No.: US 8,173,173 B2
(45) Date of Patent: May 8, 2012

(54) ANHDYROUS LACTOSE AGGLOMERATES AND THE PREPARATION THEREOF

(75) Inventors: Klaas Daniël Kussendrager, Veghel (NL); Bouwe Walsma, Renkum (NL)

(73) Assignee: Campina Nederland Holding B.V., Zaltbommel (NL)

( * ) Notice: Subject to any disclaimer, the term of this patent is extended or adjusted under 35 U.S.C. 154(b) by 865 days.

(21) Appl. No.: 11/722,968

(22) PCT Filed: Dec. 21, 2005

(86) PCT No.: PCT/NL2005/050089
§ 371 (c)(1),
(2), (4) Date: Jul. 28, 2008

(87) PCT Pub. No.: WO2006/068484
PCT Pub. Date: Jun. 29, 2006

(65) Prior Publication Data
US 2009/0081308 A1     Mar. 26, 2009

(30) Foreign Application Priority Data
Dec. 22, 2004    (EP) .................................... 04078479

(51) Int. Cl.
*A61K 9/50*     (2006.01)
(52) U.S. Cl. ........ 424/499; 424/489; 424/464; 424/451; 536/123.13; 514/777; 264/117; 127/31
(58) Field of Classification Search ........................ None
See application file for complete search history.

(56) References Cited

U.S. PATENT DOCUMENTS

| | | | |
|---|---|---|---|
| 2,182,619 A | 12/1939 | Sharp et al. | |
| 3,802,914 A | 4/1974 | Nezbed | |
| 5,534,555 A * | 7/1996 | Meggelaars et al. | 514/777 |
| 6,039,275 A * | 3/2000 | Slangen et al. | 241/17 |
| 6,306,444 B1 * | 10/2001 | Joseph | 424/725 |
| 2004/0014714 A1 | 1/2004 | Kussendrager et al. | |
| 2004/0052733 A1* | 3/2004 | Staniforth et al. | 424/46 |
| 2006/0006258 A1* | 1/2006 | Remon et al. | 241/21 |

FOREIGN PATENT DOCUMENTS

GB     2077268     12/1981

OTHER PUBLICATIONS

Shah, K.R. et al. International Journal of Pharmaceutics 357: 228-234 (2008).
Domo advertisement for Lactohale(R)—including microfine lactose (2004).

* cited by examiner

*Primary Examiner* — Robert A Wax
*Assistant Examiner* — Hasan Ahmed
(74) *Attorney, Agent, or Firm* — Browdy and Neimark, PLLC

(57) ABSTRACT

The invention relates to a process for the preparation of anhydrous lactose agglomerates, said process comprising (i) subjecting essentially anhydrous lactose primary particles comprising at least 60 wt % crystalline-lactose in a granulator to a wet granulation step at a temperature in the range of 30-100° C. using a binder solution, wherein the granulation mass is subjected to drying for at least part of the granulation step, and (ii) after-drying the granulation mass. The anhydrous lactose agglomerates thus produced comprise at least 50 wt %-lactose crystallites and have a total water content in the range of 0-1.0 wt %, which is required according to the standards laid down by the Pharmacopoeia for anhydrous lactose excipients. These agglomerates combine have excellent compactibility and flowability properties and are particularly useful as excipient in moisture-sensitive applications.

13 Claims, No Drawings

ANHDYROUS LACTOSE AGGLOMERATES AND THE PREPARATION THEREOF

TECHNICAL FIELD OF THE INVENTION

The invention relates to anhydrous lactose agglomerates, the preparation thereof, and the use of these agglomerates as an excipient (filler-binder) or diluent in tablets and capsules or as a carrier in dry powder inhalers.

BACKGROUND OF THE INVENTION

Lactose is widely used as a filler, filler-binder or diluent in tablets and capsules, and to a more limited extent in lyophilized products, infant food formulas, and as a carrier for dry powder inhalers. Worldwide, Pharmacopoeia have laid down requirements in their lactose monographs on the identity and purity of pharmaceutical grade lactose, thereby distinguishing between lactose monohydrate and anhydrous lactose. According to these pharmacopoeia, anhydrous lactose should have a water content of at most 1 wt % and is for that reason particularly useful as excipient in moisture-sensitive applications.

In solution, lactose exists as an equilibrium of approximately 60% β-lactose and 40% α-lactose, the two stereoisomers being differentiated by the orientation of the hydroxyl group at carbon atom 1 in the glucose ring of lactose. Upon crystallisation below 93.5° C. α-lactose monohydrate crystals are formed. Above 93.5° C., β-lactose crystallises.

Crystalline β-lactose is an anhydrous non-hygroscopic form meeting the aforementioned criterion of low water content. Under stringent conditions thermal dehydration or desiccation of α-lactose monohydrate crystals may also yield anhydrous modifications, in most cases a mixture of stable and unstable anhydrous lactose.

Anhydrous lactose is conventionally produced by roller drying and comprises more than 70% crystalline β-lactose, such as described by Lerk et al. in Physico-Pharmaceutical Properties of Lactose; Proceedings of the International Colloquium on Industrial Pharmacy (1983) pages 59-88. U.S. Pat. No. 3,802,914 discloses an alternative route of spraying a lactose solution onto a revolving heated drum at high temperature, thereby yielding an anhydrous lactose high in β-lactose.

GB-A-2.077.268 teaches a process for producing anhydrous stable lactose, wherein crystalline α-lactose monohydrate is introduced as a dry product into an extruder, the jacket of which is heated to a temperature above 100° C., and the lactose is then extruded. Temperatures of 162 and 164° C. are exemplified. This method yields anhydrous lactose high in β-lactose, which can be used to manufacture tablets, but it is not agglomerated, and the lactose so prepared shows relatively high bulk density and low compactibilities. Therefore, tablets prepared from the anhydrous stable lactose according to GB-A-2.077.268 can only resist pressures of 10-13 kg. These numbers can be expressed in terms of tablet strength at 10 kN compression force, as used in the application, to give a tablet strength of about 75 N.

Anhydrous β-lactose is not to be confused with spray-dried lactose as for instance disclosed in U.S. Pat. No. 3,639,170 or EP-A-239.172. Spray-dried lactose is a hygroscopic form consisting of spherical particles of small α-lactose monohydrate crystals glued together in an amorphous lactose matrix and typically containing less than 20% of β-lactose. Because of its high α-lactose monohydrate content spray-dried lactose shows limited compactibility. Moreover, its total water content of about 5 wt % makes it unsuitable for many moisture-sensitive applications.

Because of its much better compactibility compared to α-lactose monohydrate or spray-dried lactose, anhydrous β-lactose is a preferred excipient in the pharmaceutical industry. However, the fluidity of roller-dried anhydrous β-lactose is usually poor, thus resulting in a wide weight variation and inhomogeneities within the final product owing to variable fill.

In order to improve its flowability, β-lactose is therefore commonly subjected to a sieving step to remove fines and obtain a coarser grade, Pharmatose DCL22 by DMV International B.V. (Veghel, The Netherlands) being a good example thereof. A drawback of such a sieving step is that improved flowability is realised at the cost of wasting valuable finely divided material. Further, the anhydrous lactose thus obtained has only limited compactibility, especially unfavourable in formulations with a high drug dosage.

Therefore, the need exists for a process for the preparation of a directly compressible β-lactose with a high percentage of β-lactose which is anhydrous (less than 1% moisture w/w), having better compactibility properties compared to regular anhydrous β-lactose, but also exhibiting good flow characteristics, and without the loss of fines during preparation.

DESCRIPTION OF THE INVENTION

Preparation of Anhydrous Lactose Agglomerates

The invention provides a process for the preparation of anhydrous lactose agglomerates, said process comprising (i) subjecting essentially anhydrous lactose primary particles comprising at least 60 wt % crystalline β-lactose in a granulator to a wet granulation step at a temperature in the range of 30-100° C. using a binder solution, wherein the granulation mass is subjected to drying for at least part of the granulation step, and (ii) after-drying the granulation mass, to obtain anhydrous lactose agglomerates comprising at least 50 wt % β-lactose crystallites and having a total water content in the range of 0-1.0 wt %, as determined by Karl Fischer titration.

It was unexpectedly found that wet granulation of primary particles having a high β-lactose content at those conditions yields an agglomerated product in anhydrous form, despite the use of aqueous binder solutions and/or temperatures far below the crystallization temperature of β-lactose.

The anhydrous lactose agglomerates obtained in the process of the invention combine excellent compactibility properties, better than regular anhydrous primary particles having a high β-lactose content, with good flow characteristics of agglomerates, and which agglomerates meet the standards laid down by the Pharmacopoeia for anhydrous lactose excipients. A tablet produced using the anhydrous lactose agglomerates of the invention exhibits a tablet strength higher than that of tablets prepared applying lactose types commercially available.

With "wet granulation" it is understood any process in which primary powder particles are made to adhere using a granulation liquid to form larger, multiparticle entities called granules or agglomerates. These agglomerates typically have a size between 100 μm and 4 mm, depending on their subsequent use and the compaction strength required for that purpose.

Any type of wet granulation method can be used for the purpose of the invention in which the temperature and humidity during mixing and granulation are controllable parameters, and wherein it is possible to control the amount of moisture present during granulation and thereafter, to avoid rapid conversion to a glassy state.

Wet granulation preferably involves granulation times in the range of 1-120 minutes, preferably between 3 and 60 minutes, more preferably between 5 and 45 minutes. Although it is preferred to dry the granulation mass during the whole granulation time, drying for at least part of the granulation time can also achieve the desired effect. It is preferred to subject the granulation mass to drying for at least the last quarter, more preferably for at least the last half part, most preferably at least the last two-third part of the granulation time.

It is preferred to maintain the free moisture content during granulation at 0.1-10 wt %, preferably between 0.5 and 5 wt %, preferably between 1 and 4 wt %, in particular lower than 3 wt %, based on the total wet weight of the granulation mass. With "free moisture" is understood any moisture present in the granulation mass during granulation which is not present as water in the crystal lattice of the lactose.

Drying during granulation according to the invention preferably involves bringing the granulation mass into contact with hot air, by blowing hot air into the granulator. At the inlet of the granulator the hot air preferably has a relative humidity in the range of 0-25%, and preferably a temperature in the range of 30-100° C., more preferably higher than 40° C., even more preferably higher than 50° C., in particular higher than 60° C.

Knowing the temperature and relative humidity of the air at the inlet and the extent to which the granulation mass is to be dried during granulation, a person skilled in the art can easily determine the actual flow rate of the hot air for the type of granulator in use.

Wet granulation according to the invention preferably involves fluid bed granulation, which is a special type of wet granulation, wherein granulation and drying are carried out in the same chamber, and wherein drying starts while agglomerates are being formed. A bed of anhydrous lactose primary particles comprising a high β-lactose content is sprayed with binder solution from a nozzle, while simultaneously fluidising the powder particles in a stream of air. Sufficient liquid is sprayed to produce granules of the required size, at which point the spray is turned off, but the fluidizing air flow continues in an after-drying step. The combination of granulation and drying in one vessel enables better control of temperature and drying rate.

"Essentially anhydrous lactose primary particles comprising at least 60 wt % crystalline β-lactose" are meant to comprise unagglomerated lactose particles having at least 60 wt % crystalline β-lactose, based on the total dry weight of lactose. It is preferred that the β-lactose primary particles comprise at least 65 wt %, even more preferably at least 70 wt %, and most preferably at least 80 wt % of crystalline β-lactose, based on the total dry weight of lactose. The crystallinity can be determined according to standardised methods disclosed in the Pharmacopoeia. The β-lactose primary particles are preferably provided by roller drying. The anhydrous primary particles comprising a high crystalline β-lactose content will from now on be referred to as "β-lactose primary particles".

It is important to start from β-lactose primary particles having a low water content in order to produce anhydrous lactose agglomerates with the process of the present invention. The water content of the primary particles is therefore between 0 and 1.0 wt %, preferably lower than 0.5 wt %, of the total weight of the lactose particles. The water content is determined by standardised Karl Fischer titration, meaning that it comprises free water as well as water present in the lactose crystallites.

Because both amorphous lactose and α-lactose monohydrate contribute to the water level, the unagglomerated lactose particles should contain less than 10 wt % α-lactose monohydrate, preferably less than 5 wt %, based on the total dry weight of lactose, and there should be less than 10 wt %, preferably less than 5 wt % of amorphous lactose present, and most preferably there is essentially no amorphous lactose present, i.e. less than 1 wt %, based on the total dry weight of the lactose primary particles.

The rest of the total dry weight of the primary particles is formed from anhydrous crystalline α- and β-lactose, wherein no separate α and β domains can be distinguished.

There is no particular limitation to the average particle size or the particle size distribution of the β-lactose primary particles used in the process of the invention. The lactose can be used as directly obtained from the crystallization/drying step, or could be first subjected to a grinding or screening step. However, it was found that the end product benefits in terms of compactibility if the β-lactose primary particles have an average size of 60 μm or less, preferably even less than 45 μm. On the other hand, it is preferred to use particles having an average size of at least 20 μm, preferably at least 30 μm in order to achieve a compactibility as high as possible. Particle size distribution is measured with an Alpine Air Jet sieve (Hosakawa Alpine, Germany). For particles below 32 μm, laser diffraction measurement is also used (e.g. with a Malvern or a Sympatec).

During wet granulation a mix of essentially anhydrous β-lactose primary powder particles is granulated using a granulation fluid. The fluid contains a non-toxic solvent which must be volatile so that it can be removed by drying. Typical solvents include water, ethanol and isopropanol, and combinations thereof. The granulation fluid preferably contains a binder or binding agent dissolved therein, which binder ensures particle adhesion once the granule is dry. For reasons of convenience, the granulation fluid is also referred to herein as "binder solution".

It was now found that in the granulation process it is beneficial to use lactose in the binder solution, preferably in the form of a lactose solution, more preferably as an aqueous lactose solution. By bringing the β-lactose primary particles into contact with a binder solution comprising lactose during wet granulation, the binding between the β-lactose primary powder particles and therewith the strength of the agglomerates is enhanced. It is preferred to add the binder solution to the β-lactose primary particles stepwise or continuously, most preferably continuously, wherein the moisture supply rate is chosen such that it roughly equals the rate at which free moisture disappears again from the granulator due to drying. Overall, the free moisture content stays within the abovementioned limits, more preferably it remains about constant during supply of the binder solution.

The lactose solution preferably comprises between 5 and 60 wt % of lactose, based on the total weight of the binder solution, and more preferably between 10 and 40 wt %. If the lactose concentration in the binder solution is above 60 wt %, the solution becomes very viscous and spraying becomes difficult. Moreover, above 60%, the solution becomes supersaturated, for instance leading to spontaneous crystallization of α-lactose monohydrate at temperatures below 93.5° C. This would unfavourably affect the water content of the end product.

Where the lactose agglomerates are to be applied as a carrier in dry powder inhalers, a lower compaction strength of the granulates may be required. This is achieved by applying lower concentrations of lactose in the binder solution, preferably at most 10 wt % of lactose, based on the total solution weight, more preferably at most 5 wt %, in particular less than 1 wt %, most preferably the binder solution is essentially free of lactose.

The binder solution can further comprise other saccharides, such as sugar alcohols, cellulose and/or cellulose derivatives. Tablets of an appreciably higher hardness are obtained for anhydrous lactose agglomerates which are produced by applying a binder solution comprising a mixture of lactose, cellulose and sugar alcohols, particularly mannitol, sorbitol, xylitol, lactitol, but also mixtures of such alcohols, for instance obtained by hydrogenation of starch hydrolysates which comprises a mixture of mono-, di-, tri- and polysaccharides. If sugar alcohols are present in the binder solution, a concentration of 1-15 wt %, calculated on the total dry weight of the solution, is preferred. Cellulose can be present in an amount of 0-40 wt % of the total dry weight of the binder solution. In another embodiment cellulose and/or sugar alcohols are provided together with the β-lactose primary particles, for instance as a homogenous mixture obtained by roller drying lactose, cellulose and sugar alcohols as disclosed in U.S. Pat. No. 5,534,555.

According to the invention, mixing or spraying of the β-lactose primary particles with the binder solution is performed at a temperature of at least 30° C. Before being introduced into the granulation process, the binder solution preferably has a temperature in the range of 30 to 100° C., more preferably 40-90° C.

The actual granulation takes place at a temperature between 30 and 100° C., preferably between 40 and 90° C. This may for instance be achieved by introducing a pre-heated flow of air into the granulation vessel. At higher temperatures colour instabilities and discoloration, i.e. yellowing, can arise. It is further preferred to keep the relative humidity of the pre-heated flow of air in the range of 0-25%. In the preferred case of using a binding solution comprising lactose, the weight ratio of the β-lactose primary particles to the amount of lactose present in the binding solution is preferably chosen in the range of 1.5:1-50:1, more preferably in the range of 4:1-20:1.

The lactose agglomerates obtained from the granulation step exhibiting a total water content higher than the desired value in the end product are subjected to an after-drying step, preferably involving a temperature in the range of 40-100° C., preferably less than 90° C., and bringing the granulation mass into contact with an air flow at low relative humidity, preferably in the range of 0-25%, in accordance with the granulation conditions. After-drying times typically involve less than 1 hour, preferably from 1 to 30 minutes, even more preferably from 2 to 15 minutes. These after-drying conditions are less stringent than the drying conditions known from conventional wet granulation techniques, where it is not unusual to dry for periods of 16 hours.

In the preferred embodiment of a fluidised bed granulation treatment drying during granulation is achieved by means of an air flow with an inlet relative air humidity of at most 25% and preferably at an inlet air temperature which is at least equal to or higher than the temperature in the fluid bed. It is preferred that the air flow during after-drying has a lower flow rate than the air flow used for drying during granulation. The actual flow rates during granulation and after-drying are dependent on the dimensions and type of granulator. In the fluidiser, agglomerates having a total water content higher than 1.0 wt % are after-dried until they have a total water content in the range of 0-1.0 wt %, preferably lower than 0.5 wt %, based on the total weight of the agglomerates, and wherein the water content is determined by Karl Fischer titration.

After granulation and drying, the dried mass can be forced through a sieve. An optional subsequent screening or milling stage breaks agglomerates or granules. Fines generated by milling may be recycled back through the granulator or compactor. These sieving, screening and milling steps, in combination with the actual granulation time, quantity and feeding time of the binder, will enable the skilled person to adapt the average size and size distribution of the anhydrous lactose agglomerates to the strength required according to the application.

Anhydrous Lactose Agglomerates

The invention further provides anhydrous lactose agglomerates comprising at least 50 wt %, preferably at least 60 wt %, more preferably between 70 and 80 wt % β-lactose crystallites held together in a matrix of predominantly anhydrous crystalline α- and β-lactose, the amount being based on the total dry weight of the agglomerates. In the matrix the crystalline α- and β-lactose forms can not be distinguished from one another, and where individual β-lactose crystallites are observed, they are considered to contribute to the discontinuous phase.

The total amount of anhydrous α-lactose in the agglomerates is preferably lower than 40 wt %, more preferably lower than 30 wt %, and most preferably lower than 20 wt %, based on the total dry weight of the agglomerates.

The water content of the anhydrous lactose agglomerates is between 0 and 1.0 wt %, preferably lower than 0.5 wt %, of the total weight of the agglomerates. The water content is determined by standardised Karl Fischer titration, meaning that it comprises free water as well as water present in the lactose crystallites. Because both amorphous lactose and α-lactose monohydrate contribute to the water content, the amount of amorphous lactose present in the agglomerates should be less than 10 wt %, preferably less than 5 wt %, based on the total dry weight of the agglomerates. It is most preferred that the amount of amorphous lactose present in the agglomerates is less than 1 wt %, based on the total dry weight of the agglomerates. Further, for the same reasoning, the amount of α-lactose monohydrate should be less than 10 wt %, preferably less than 5.0 wt %, most preferably less than 1 wt %, based on the total dry weight of the agglomerates.

The anhydrous lactose agglomerates obtainable according to the process of the invention are characterised by a broad size distribution in comparison to spray-dried granules produced from the same batch of primary particles. The size distribution is determined similarly to that of the primary particles using an Alpine Air Jet sieve. The agglomerates typically have a size between 50 and 4000 µm, more preferably between 100 and 1000 µm, albeit that the actual distribution is dependent both on the size distribution of the β-lactose primary particles used, and the agglomeration process conditions in the preparation. The average size of the agglomerates is typically at least 5 times larger than the average size of those β-lactose primary particles, preferably at least 100 µm. The agglomerates comprise on average at least 5 crystallised β-lactose domains, preferably of regular, non-spherical shape, clustered in a rather dense crystalline matrix of anhydrous α/β-lactose. This matrix is a substantially homogeneous phase in which no separate α and β domains can be distinguished.

The agglomerates of the invention possess greater porosity than granules prepared by wet granulation processes known in the art, and its surface is covered by a film of binding agent. It is found that the granule fractions prepared by the granulation process of the invention show relatively lower bulk densities and relatively higher compactibilities as compared with agglomerates produced by agglomeration techniques at wet conditions, wherein drying is performed only after granulation.

The anhydrous lactose agglomerates according to the invention preferably have a standard poured bulk or bed density between 250 and 600, more preferably between 300 and 550 g/l, and preferably a tapped bed or bulk density between 250 and 800, more preferably between 400 and 750 g/l, as measured according to US Pharmacopoeia 25 page 1981.

The strength of the agglomerates may be determined using a modified laser diffraction measurement. The robustness or firmness of the aggregates is tested by introducing them in the laser diffraction measurement system in a certain airflow under various pressures, e.g. at 0.5, 3 and 5 bar, for a certain period of time. The decrease in average particle size measured after treatment at various pressures, is a measure for the robustness or stability of the agglomerates. An instrument which can be used for this method is e.g. the Sympatec Helos from Sympatec GmbH (Germany), installed with a R5 lens (0.5-875 μm) and equipped with a RODOS dry dispersing system in combination with a VIBRI vibratory powder feeder.

The flowability of the agglomerates may be determined using a so-called Flodex apparatus (Hanson, USA), which is a cylinder in which a disc is fitted at the lower end, through which a powder can flow. The disc can have openings varying between 4 to 34 mm, depending on the powder type. An amount of powder of agglomerates is placed in the cylinder, the closing plate is removed and it is observed whether flow occurs. The flowability value is the minimum disc aperture (diameter) at which flow still occurs, based on three consecutive measurements.

The compaction properties of the tablets made with the agglomerates are determined as the tablet crushing strength. Tablets are prepared using a Kilian rotary press (Kilian, Germany) for making 250 mg tablets with a 9 mm diameter by applying a compaction force of 5-20 kN. The tablets prepared using the agglomerates of the invention preferably show a compact strength between 80 and 200 N, preferably higher than 90 N, more preferably higher than 100 N at a compaction force of 10 kN, whereas for the unagglomerated particles typically values as high as 65-75 N are observed.

Prior to tabletting, the agglomerate powder can be lubricated by mixing with an appropriate amount of lubricating agent, e.g. stearic acid or the salts thereof (for instance magnesium stearate). The amount of lubricating agents used is between 0.1 and 2 wt % based on the weight of the agglomerates.

The anhydrous lactose agglomerates may further comprise ingredients other than lactose, for instance cellulose and/or sugar alcohols that are used in the preparation as a binder.

Use of Anhydrous Lactose Agglomerates

The invention also relates to the use of the anhydrous lactose agglomerates according to the invention as a diluent, carrier or filler for pharmaceutical applications, including tablets, injectables, capsules, sachets, pellets and dry powder inhalers. The anhydrous lactose agglomerates are especially considered beneficial for use with a moisture-sensitive active substance.

The invention further relates to a tablet, injectable, capsule, sachet, pellet or dry powder inhaler comprising the anhydrous lactose agglomerates of the invention, either alone or in combination with other diluents, carriers or fillers.

Example 1a

Preparation of Agglomerated Anhydrous β-Lactose Particles

Anhydrous β-lactose (DCL 21 from DMV International, The Netherlands) was milled using a mill from Retsch (Germany) to an average particle size of 40 μm, as measured by laser diffraction using a Sympatec Helos (Sympatec GmbH, Germany). Separately, a 20% w/w lactose solution in water was prepared. An amount of 400 gram of the milled β-lactose was placed in an Aeromatic Strea-1 Granulator from Aeromatic AG (Switzerland), and agglomerated with an amount of 102 gram of the lactose solution per 400 gram milled β-lactose. The lactose solution was added at a rate of 8.5 g/min at a temperature of 45° C. The granulation took place at a temperature of 50° C., with an air flow of about 0.7 $m^3$/min. The temperature of the inlet air was 85° C. The agglomeration time was about 12 minutes, the subsequent after-drying time about 5 minutes.

The thus obtained agglomerated lactose was sieved with a screen having a cutoff of 500 μm to remove coarse particles. The particles with a size below 500 μm were collected.

Example 1b

Preparation of Agglomerated Anhydrous β-Lactose Particles

Anhydrous β-lactose (DCL 21 from DMV International, The Netherlands) was milled using a mill from Retsch to an average particle size of 30 μm (measured by laser diffraction using a Sympatec Helos). Separately, a 10% w/w lactose solution was prepared. An amount of 400 gram of the milled β-lactose was placed in an Agglomaster (Hosokawa Micron B.V., The Netherlands), and agglomerated with an amount of 125 gram of the lactose solution per 400 gram milled lactose. The lactose solution was added at a rate of 11 g/min at a temperature of 35° C. The granulation took place at a temperature of 45° C., with an air flow of about 0.8 $m^3$/min. The temperature of the inlet air was 90° C. Time of agglomeration: 11 minutes, after-drying time: 7 minutes.

The thus obtained agglomerated lactose was sieved with a screen having a cutoff of 350 μm to remove coarse particles. The particles with a size below 350 μm were collected.

Example 1c

Preparation of Agglomerated Anhydrous D-Lactose Particles

Anhydrous β-lactose (DCL 21 from DMV International, The Netherlands) was sieved through a 80 μm sieve and the particles below 80 μm were collected. The average particle size was 26 μm (measured by laser diffraction using a Sympatec Helos). Separately, a 35% w/w lactose solution was prepared. An amount of 400 gram of the fine β-lactose was placed in a fluid bed agglomerator, Agglomaster (Hosokawa Micron B.V., The Netherlands), and agglomerated with an amount of 220 gram of the lactose solution per 400 gram fine β-lactose. The lactose solution was added at a rate of 20 g/min at a temperature of 85° C. The granulation took place at a temperature of 50° C., with an air flow of about 0.8 $m^3$/min. The temperature of the inlet air was 90° C. Time of agglomeration: 11 minutes, after-drying time: 10 minutes.

The thus obtained agglomerated lactose was sieved with a screen having a cutoff of 400 μm to remove coarse particles. The particles with a size below 400 μm were collected.

Example 2

Preparation of Anhydrous D-Lactose Agglomerates Using Water as a Binder Solution Anhydrous β-lactose (DCL 21 from DMV International, The Netherlands) was milled using a mill from Retsch to an average particle size of 40 µm (measured by laser diffraction using a Sympatec Helos). An amount of 400 gram of the milled beta-lactose was placed in an Aeromatic Strea-1 Granulator, and agglomerated with an amount of 52 gram water per 400 gram lactose. The water was added at a rate of 7.5 g/min at a temperature of 30° C. The granulation took place at a temperature of 40° C., with an air flow of about 0.6 m³/min. The temperature of the inlet air was 80° C. Time of agglomeration: 7 minutes, after-drying time: 8 minutes.

The thus obtained agglomerated lactose was sieved with a screen having a cutoff of 500 µm to remove coarse particles. The particles with a size below 500 µm were collected.

Comparative Example

Pharmatose DCL 21 was milled to an average particle size of 30 µm, and was wet granulated in a Kenwood mixer (Kenwood Ltd, UK) at 20° C. using water (10 gram/100 gram lactose). After a mixing time of 3 minutes, the wet agglomerates were collected and screened using a 1.6 mm screen, and dried in a ventilated oven at 60° C. for at least 16 hours. The dried agglomerates were screened again using a 500 µm screen. Upon measurement of the moisture content, it appeared that the agglomerates contained about 2.5 wt % of water and were therefore found to be unsuitable as excipient in formulations of moisture sensitive drugs. No further tabletting experiments were contemplated.

The agglomerated lactose prepared according to examples 1a, 1b, 1c and 2 were analyzed. The test results are compared with those of Pharmatose DCL 21.

The agglomerated lactose prepared according to examples 1a, 1b, 1c and 2 were tabletted using a Kilian rotary press (Kilian, Germany), making 250 mg tablets with a 9 mm diameter by applying a compaction force of 10 kN. Prior to tabletting the powders were lubricated for 2 minutes by mixing with 1% Magnesium stearate. Pharmatose DCL 21 was tabletted in the same way. The tablets were tested for tablet strength.

TABLE 1

|  | DCL 21 | Ex. 1a | Ex. 1b | Ex. 1c | Ex. 2 |
| --- | --- | --- | --- | --- | --- |
| Water KF (wt %)* | 0.35 | 0.56 | 0.45 | 0.58 | 0.38 |
| Poured bed density (g/l)** | 680 | 459 | 355 | 437 | 544 |
| Tapped bed density (g/l)** | 880 | 596 | 455 | 542 | 713 |
| α-lactose (wt %) | 19.4 | 19.3 | 19.0 | 17.4 | 18.0 |
| β-lactose (wt %) | 80.6 | 80.7 | 81.0 | 82.6 | 82.0 |
| Tablet strength at 10 kN (N) | 75 | 105 | 120 | 123 | 105 |
| Flodex index (mm)*** | 20 | 6 | 6 | 5 | 6 |

*KF = Karl Fischer titration;
**according to US Pharmacopoeia 25, page 1981;
***0-6 mm excellent flow, 7-10 mm good flow, 11-20 mm moderate flow, >20 mm poor flow

The invention claimed is:

1. A process for preparing anhydrous lactose agglomerates, comprising:
   (i) subjecting essentially anhydrous lactose primary particles comprising at least 60 wt % crystalline β-lactose in a granulator to wet granulation at a temperature of 30°-100° C. using a binder solution, to obtain a granulation mass,
   (ii) drying the granulation mass during at least part of the granulation step (i), by blowing hot air having a relative humidity of 0-25% and a temperature of at least 50° C. at the inlet of the granulator and into the granulator,
      wherein during the wet granulation, free moisture content is maintained between 0.1 and 10 wt %, based on the total wet weight of the granulation mass, and
   (iii) after drying, obtaining said anhydrous lactose agglomerates which comprise at least 50 wt % β-lactose crystallites and a total water content in the range of 0-1.0 wt %, as determined by Karl Fischer titration.

2. The process according to claim 1, wherein the free moisture content during granulation is maintained at between 0.5 and 5 wt %, based on the total weight of the granulation mass.

3. The process according to claim 1, wherein said drying during granulation comprises bringing the granulation mass into contact with hot air is at a temperature of 60° C. to 100° C. at the inlet of the granulator.

4. The process according to claim 1, wherein the binder solution comprises lactose.

5. The process according to claim 4, wherein the lactose is present at a concentration between 5 wt % and 60 wt %.

6. The process according to claim 4, wherein the weight ratio of the anhydrous lactose primary particles to the lactose in the binder solution is from 1.5 to 50.

7. The process according to claim 1, wherein the wet granulation comprises fluid bed granulation.

8. Anhydrous lactose agglomerates comprising at least 50 wt % β-lactose crystallites and a total water content of 0-1.0 wt %, as determined by Karl Fischer titration, which agglomerates are prepared by the process of claim 1.

9. Anhydrous lactose agglomerates according to claim 8, which have a poured bulk density of between 250 and 600 g/l.

10. Anhydrous lactose agglomerates according to claim 8, which have a tapped bed density of between 250 and 800 g/l.

11. A tablet, capsule or dry powder inhaler comprising the anhydrous lactose agglomerates according to claim 8.

12. A tablet, capsule or dry powder inhaler comprising anhydrous lactose agglomerates that are prepared by the process of claim 7.

13. A tablet, capsule or dry powder inhaler comprising anhydrous lactose agglomerates that are prepared by the process of claim 1.

* * * * *